US005780433A

United States Patent [19]
McIntosh et al.

[11] Patent Number: 5,780,433
[45] Date of Patent: Jul. 14, 1998

[54] USE OF α-CONOTOXIN MII TO TREAT DISORDERS RESULTING FROM NICOTINE STIMULATED DOPAMINE RELEASE

[75] Inventors: J. Michael McIntosh; Jennifer M. Kulak; Doju Yoshikami; Baldomero M. Olivera, all of Salt Lake City, Utah

[73] Assignee: University of Utah Research Foundation, Salt Lake City, Utah

[21] Appl. No.: 761,674

[22] Filed: Dec. 6, 1996

[51] Int. Cl.⁶ .................................................. A61K 38/00
[52] U.S. Cl. ................................................ 514/13; 514/813
[58] Field of Search ........................................ 514/13, 813

[56] References Cited

U.S. PATENT DOCUMENTS

| 5,595,972 | 1/1997 | Olivera et al. | 514/13 |
| 5,633,347 | 5/1997 | Olivera et al. | 536/324 |

OTHER PUBLICATIONS

Tennant et al. NIDA Res. Monogr., 49, 239, 1984.
Tennant et al. NIDA Res. Monogr. 55, 291–297, 1984.
Rose et al. Pharmacol. Bioch. & Behav. 32, 933–938, 1989.
Rose et al. Clin. Pharmacol. & Therapeutics. 56(1), 86–98, Jul. 1994.
Benwell et al. Br. J. Pharmacol. 117, 743–749, Feb. 1996.
Corrigall et al. Psychopharmacol., 99, 473–478, 1989.
Glick et al. Nature. 227, 969–970, 1970.
Stolerman et al. Psycho Pharmacologia. 28, 247–259, 1973.
Harvey et al. 26 Annual Meeting of Society for Neurosc. 22 (1–3) p. 1259, Nov. 1996.
Cartier et al. J. Biol. Chem. 271 (13) pp. 7522–7528, Mar. 29, 1996.
Corrigall et al. Psychopharmacology, 104, 171–176, 1991.
Corrigall et al. Brain Research. 653, 278–284, 1994.

*Primary Examiner*—Rebecca Cook
*Attorney, Agent, or Firm*—Rothwell, Figg, Ernst & Kurz, P.C.

[57] ABSTRACT

Neuronal nicotinic acetylcholine receptors (nAChRs) are believed to mediate nicotine addiction. In addition, stimulation of nAChRs modulates release of neurotransmitters including dopamine, norepinephrine and serotonin. Thus, pharmacological manipulation of nicotinic receptors has implications for a wide variety of disorders including psychotic, mood, movement and cognitive. For most nAChRs, there are no subtype selective ligands. However, α-conotoxin MII, a small peptide from the carnivorous marine snail *Conus magus*, was recently isolated. This peptide has been shown to be a specific antagonist for α3β2 nicotinic receptors. The peptide potently blocks part, but not all, of nicotine-stimulated dopamine release from rat brain striatal synaptosomes. In contrast it has no effect on potassium stimulated dopamine release. Other α-conotoxins specifically target distinct neuronal nAChR subtypes. α-Conotoxins thus represent new lead compounds for CNS disorders.

5 Claims, 6 Drawing Sheets

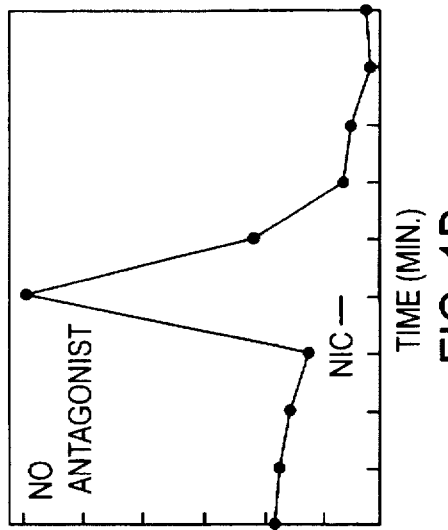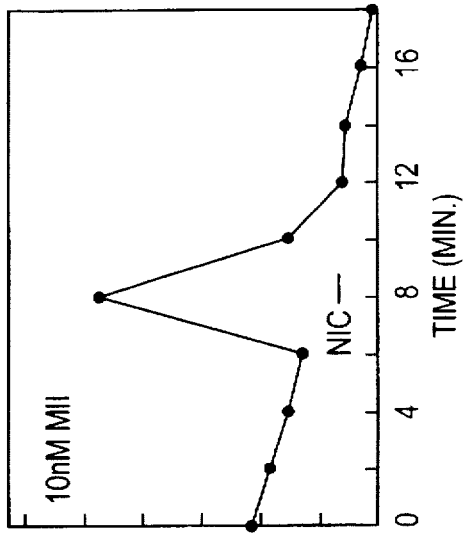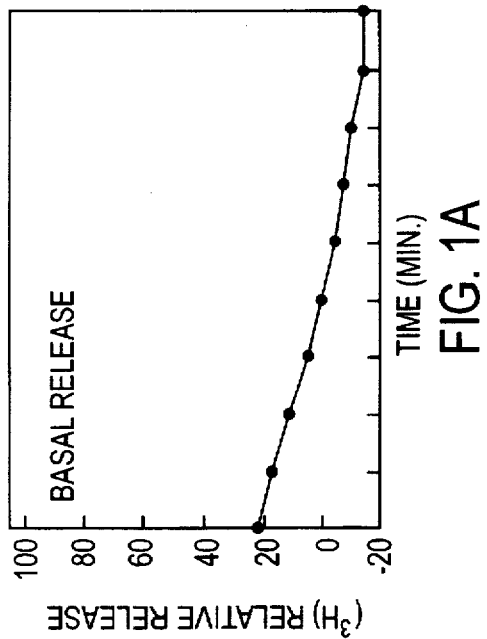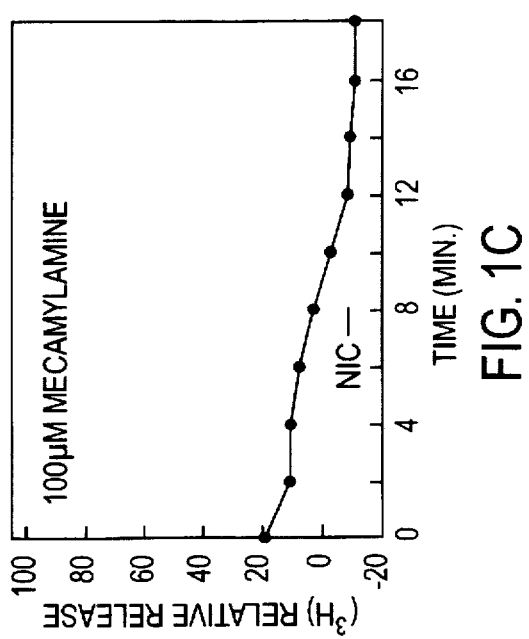

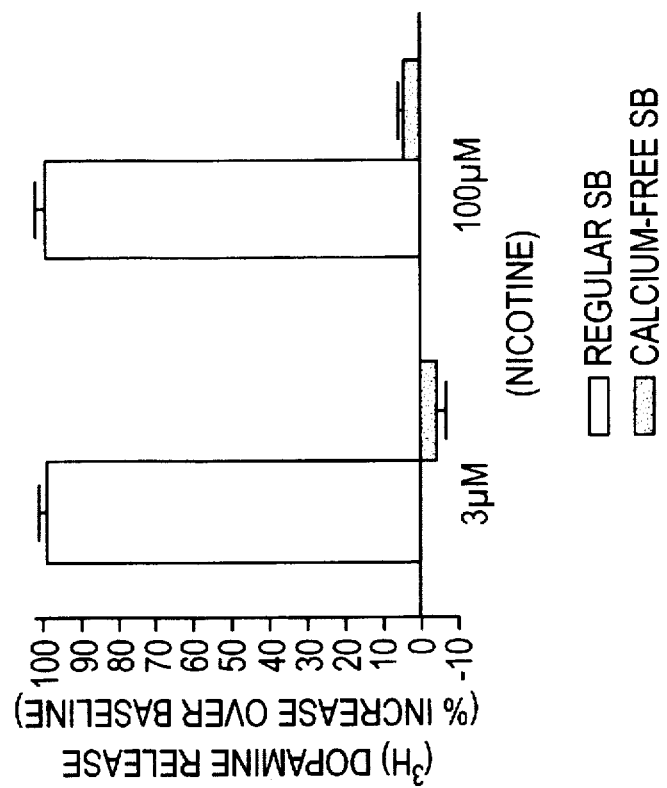
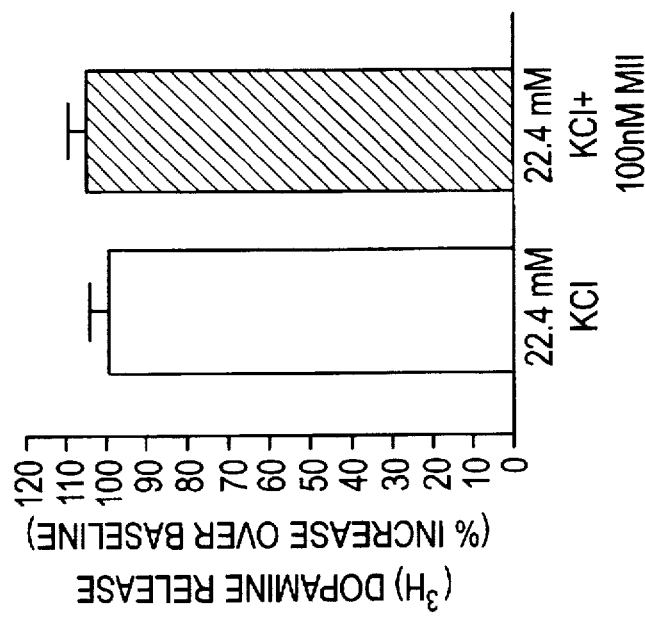
FIG. 3A
FIG. 3B

USE OF α-CONOTOXIN MII TO TREAT DISORDERS RESULTING FROM NICOTINE STIMULATED DOPAMINE RELEASE

This invention was made with Government support under Grant Nos. MH 53631 and GM 48677, awarded by the National Institutes of Health, Bethesda, Md. The United States Government has certain rights in the invention.

BACKGROUND OF THE INVENTION

The present invention relates to the use of the α-conotoxin MII to treat disorders that are caused by the action of nicotine stimulating nicotinic acetylcholine receptors (nAChRs). When nicotine binds to certain subtypes of nAChRs it induces the release of dopamine. The α-conotoxin MII has now been found to be a specific neuronal nAChR antagonist and can limit nicotine stimulated dopamine release. Cigarette smoke contains nicotine, which acts upon nAChRs resulting in dopamine release, which is effectively a reward. Treatment with α-conotoxin MII will block the nicotinic receptors thereby preventing the release of dopamine and will block the reward. Consequently α-conotoxin MII can be used to aid persons to quit smoking.

A second aspect of the invention is that α-conotoxin MII is useful for the treatment of various psychoses, e.g., schizophrenia and mood disorders. Presently the standard treatment for psychosis is to block the post-synaptic dopamine recognition. The equivalent effect is be achieved by blocking an earlier step, specifically, by blocking the presynaptic release of dopamine. α-Conotoxin MII is effective at preventing the presynaptic release of dopamine because it is a nAChR antagonist.

The publications and other materials used herein to illuminate the background of the invention, or to provide additional details respecting the practice, are incorporated by reference and for convenience are respectively grouped in the appended List of References.

Neuronal nicotinic acetylcholine receptors have been implicated in the treatment or pathophysiology of several neuropsychiatric disorders including Alzheimer's disease (Nordberg et al., 1990; Nordberg et al., 1989), Parkinson's disease (Grandinetii et al., 1994; Janson et al., 1988; Reavill, 1990), Tourette's syndrome (Sandberg et al., 1988; Sandberg et al., 1989) and schizophrenia (Adler et al., 1993; Luntz-Leybman et al., 1992). In addition, nicotine, a psychoactive constituent of tobacco smoke, reinforces smoking behavior through its effects on nAChRs (Stolerman and Jarvis, 1995). The central effects of nicotine are complex and appear to be mediated by several nAChR subtypes, but it is not known which subtype(s) is responsible for the reinforcing effects of nicotine.

Neuronal nicotinic acetylcholine receptors are believed to be heteropentameric ion channel complexes generally requiring at least two different subunits (an α and a β). Molecular data indicate that in the mammalian central nervous system there exists a large number of different nAChR subunits. To date, seven different α subunits (α2–α7, α9) and three different β subunits (β2–β4) have been defined by cloning.

Currently available neuropsychiatric medications work primarily by blocking neurotransmission through postsynaptic receptor antagonism or by blocking neurotransmitter re-uptake or catabolism (Schatzberg et al., 1995). While postsynaptic nAChRs have been recognized for some time, more recent data have demonstrated the presence of presynaptic neuronal nAChRs. Agonist stimulation of presynaptic nAChRs induces neurotransmitter release. Nicotinic agonists have been shown to elicit the release of several different neurotransmitters, including dopamine from striatum and frontal cortex (El-Bizri and Clarke, 1994; Grady et al., 1992; Rapier et al., 1988); norepinephrine from hippocampus (Clarke and Reuben, 1996; Rowell and Winkler, 1984; Sacaan et al., 1995; Wilkie et al., 1993); glutamate from cortex, medial habenula nucleus and hippocampus (McGehee and Role, 1995; Vidal and Changeux, 1993; Gray et al., 1996); GABA from interpeduncular nucleus (Mulle et al., 1991) and acetylcholine for cortex and hippocampus (Lapchak et al., 1989; Rowell and Winkler, 1984).

In addition, it appears that distinct subtypes of presynaptic nAChRs regulate the release of different neurotransmitters. For example, nicotine-stimulated glutamate and acetylcholine release are blocked by α-bungarotoxin suggesting that these nAChRs include an α7 subunit (McGehee and Role, 1995). In contrast, nicotine-stimulated dopamine release is not blocked by α-bungarotoxin (Grady et al., 1992). Furthermore, the nAChRs modulating norepinephrine release pharmacologically differ from those modulating the release of glutamate, acetylcholine or dopamine (Clarke and Reuben, 1996; Sacaan et al., 1995).

The possibility of selectively modulating the presynaptic release of specific neurotransmitters has significant therapeutic applications. For example, current antipsychotic medications inhibit dopamine signaling by blocking postsynaptic dopamine receptors. Block of presynaptic nAChRs will attenuate but not abolish dopamine signaling, a result which leads to antipsychotic effects but with fewer side effects than complete postsynaptic dopamine receptor blockade. Another example of a therapeutic application is tobacco addiction. Studies of nicotine self-administration in animal models suggest that block of nAChRs decreases the reinforcing properties of nicotine.

Despite the importance of nAChRs that modulate dopamine release, the particular subtypes which underlie this release have been difficult to determine despite substantial investigation. This difficulty is due in part to the lack of subtype-specific ligands. The use of the newly isolated α-conotoxin MII, a specific neuronal nAChR antagonist to examine nAChRs involved in nicotine-stimulated neurotransmitter release is described here.

SUMMARY OF THE INVENTION

The present invention relates to the use of the α-conotoxin MII to treat disorders that are caused by the action of nicotine stimulating nicotinic acetylcholine receptors (nAChRs). When nicotine binds to certain subtypes of nAChRs it induces the release of dopamine. The α-conotoxin MII has now been found to be a specific neuronal nAChR antagonist and can limit nicotine stimulated dopamine release. Cigarette smoke contains nicotine which acts upon nAChRs resulting in dopamine release which is effectively a reward. Treatment with α-conotoxin MII will block the nicotinic receptors thereby preventing the release of dopamine and will block the reward. Thus α-conotoxin MII can be used to aid persons to quit smoking.

A second aspect of the invention is that α-conotoxin MII is useful for the treatment of various psychoses. Presently the standard treatment for psychosis is to block the post-synaptic dopamine recognition. The equivalent effect can be achieved by blocking an earlier step, specifically, by blocking the presynaptic release of dopamine. α-Conotoxin MII is effective at preventing the presynaptic release of dopamine because it is a nAChR antagonist.

BRIEF DESCRIPTION OF THE FIGURES

FIGS. 1A–D show the results of the synaptosomal assay. Synaptosomes were preloaded with [$^3$H]-dopamine and tested for nicotine-stimulated release, using 3 µM nicotine. FIG. 1A shows the basal release of [$^3$H]-dopamine in the absence of nicotine. FIG. 1B shows the nicotine-stimulated release of [$^3$H]-dopamine. FIG. 1C shows the block of nicotine-stimulated dopamine release by mecamylamine, a non-selective nicotinic antagonist. FIG. 1D shows that 10 nM MII blocks a fraction of nicotine-stimulated dopamine release.

FIG. 3A shows that α-conotoxin MII does not block K$^+$ (voltage)-stimulated dopamine release. Thus MII's effects are selective for nicotine-stimulated release.

FIG. 3B shows that nicotine-stimulated dopamine release is calcium dependent as expected of synaptic neurotransmitter release.

DETAILED DESCRIPTION OF THE INVENTION

Figure 2:
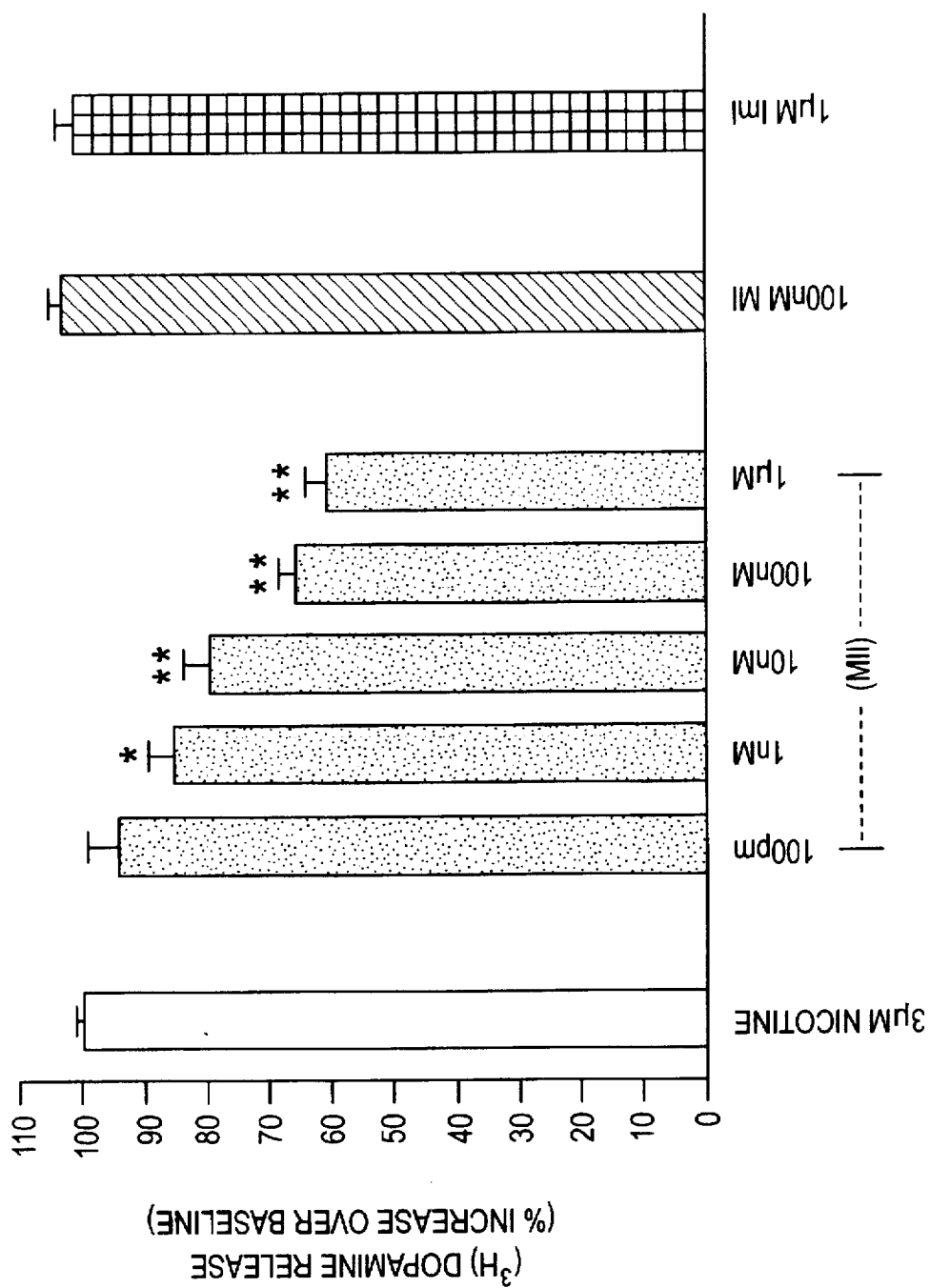
FIG. 2 shows that α-conotoxin MII blocks a part but not all of nicotine-stimulated dopamine release. MII was tested using the synaptosomal assay. At low concentrations (i.e. 0.1–10 nM) MII is specific for α3β2 containing receptors. At higher concentrations (100 nM–1 µM) MII likely blocks additional subtypes of nAChRs. Sterically related a-conotoxins ImI (selective for α7 nAChRs) and α-conotoxin MI (selective for α1-containing nAChRs) do not block nicotine-stimulated dopamine release.

The present invention is directed to the finding that (α-conotoxin MII is an antagonist of a specific subset of nAChRs and limits the nicotine stimulated release of dopamine. Dopamine is a neurotransmitter. At low concentrations α-conotoxin MII selectively blocks the α3β2 subtype of nicotinic receptor. This selective activity can be used advantageously to inhibit dopamine release by nerve cells that contain this type of nAChR. Such presynaptic blockage of dopamine may be used to treat various disorders that are connected to these receptors. These include the use of α-conotoxin MII to aid in quitting smoking and in the treatment of psychosis.

Neuronal nicotinic acetylcholine receptors have been implicated in the treatment or pathophysiology of several neuropsychiatric disorders including Alzheimer's disease (Nordberg et al., 1990; Nordberg et al., 1989), Parkinson's disease (Grandinetii et al., 1994; Janson et al., 1988; Reavill, 1990), Tourette's syndrome (Sandberg et al., 1988; Sandberg et al., 1989) and schizophrenia (Adler et al., 1993; Luntz-Leybman et al., 1992). In addition, nicotine, a psychoactive constituent of tobacco smoke, reinforces smoking behavior through its effects on nAChRs. The central effects of nicotine are complex and appear to be mediated by several nAChR subtypes, but it is not known which subtype(s) is responsible for the reinforcing effects of nicotine.

Neuronal nicotinic acetylcholine receptors are believed to be heteropentameric ion channel complexes generally requiring at least two different subunits (an α and β). Molecular data indicate that in the mammalian central nervous system there exists a large number of different nAChR subunits. To date, seven different a subunits (α2–α7, α9) and three different β subunits (β2–β4) have been defined by cloning.

Currently available neuropsychiatric medications work primarily by blocking neurotransmission through postsynaptic receptor antagonism or by blocking neurotransmitter re-uptake or catabolism (Schatzberg et al., 1995). While postsynaptic nAChRs have been recognized for some time, more recent data have demonstrated the presence of presynaptic neuronal nAChRs. Agonist stimulation of presynaptic nAChRs induces neurotransmitter release. Nicotinic agonists have been shown to elicit the release of several different neurotransmitters, including dopamine from striatum and frontal cortex (El-Bizri and Clarke, 1994; Grady et al., 1992; Rapier et al., 1988); norepinephrine from hippocampus (Clarke and Reuben, 1996; Rowell and Winkler, 1984; Sacaan et al., 1995; Wilkie et al., 1993); glutamate from cortex, medial habenula nucleus and hippocampus (McGehee and Role, 1995; Vidal and Changeux, 1993; Gray et al., 1996); GABA from interpeduncular nucleus (Mulle et al., 1991) and acetylcholine for cortex and hippocampus (Lapchak et al., 1989; Rowell and Winkler, 1984).

In addition, it appears that distinct subtypes of presynaptic nAChRs regulate the release of different neurotransmitters. For example, nicotine-stimulated glutamate and acetylcholine release are blocked by α-bungarotoxin suggesting that these nAChRs include an α7 subunit (McGehee and Role, 1995). In contrast, nicotine-stimulated dopamine release is not blocked by α-bungarotoxin (Grady et al., 1992). Furthermore, the nAChRs modulating norepinephrine release pharmacologically differ from those modulating the release of glutamate, acetylcholine or dopamine (Clarke and Reuben, 1996; Sacaan et al., 1995).

The possibility of selectively modulating the presynaptic release of specific neurotransmitters has significant therapeutic applications. For example, current antipsychotic medications inhibit dopamine signaling by blocking postsynaptic dopamine receptors. Block of presynaptic nAChRs will attenuate but not abolish dopamine signaling, a result which leads to antipsychotic effects but with fewer side effects than complete postsynaptic dopamine receptor blockade. Another example of a therapeutic application is tobacco addiction. Studies of nicotine self-administration in animal models suggest that block of presynaptic nAChRs decreases the reinforcing properties of nicotine.

Experiments presented below show that α-conotoxin MII blocks part but not all of nicotine-stimulated dopamine release. In contrast, (α-conotoxin MII does not block depolarization-induced dopamine release indicating its specificity for nicotine-stimulated neurotransmitter release. α-Conotoxin MII blocks α3β2 nAChRs expressed in Xenopus oocytes with an IC$_{50}$ of 0.5 nM. α-Conotoxin MII also blocks other nAChR subunit combinations but with affinities that are two to four orders-of-magnitude higher, with the order of potency: α3β2>>α7>α4β2>α2β2≡α3β4>α1β1δγ>α4β4≧α2β2 (Cartier et al., 1996a; Cartier et al., 1996b). At low nanomolar concentrations, e.g., 1 and 10 nM, α-conotoxin MII blocks essentially only α3β2 receptors, strongly suggesting that the block of nicotine-stimulated dopamine release seen at these α-conotoxin MII concentrations is due to block of native α3β2-containing nAChRs. The increased block of nicotine-stimulated dopamine release seen at 100 nM and 1 μM MII may reflect block of non-α3β2 nAChR subtypes. Thus, these results suggest that some but not all of nicotine-stimulated dopamine release is due to α3β2-containing nAChRs. Other nAChR subtypes may therefore mediate the remainder of the response, i.e., more than one subtype of neuronal nAChR is responsible for nicotine-stimulated dopamine release.

In contrast to nicotine-stimulated dopamine release, low nanomolar concentrations of MII do not block nicotine-stimulated synaptosomal norepinephrine release. At higher concentrations (i.e., 1 μM) α-conotoxin MII produces significant block of nicotine-stimulated norepinephrine release, consistent with block of non-α3β2-containing receptors. Thus the role of α3β2-containing nAChRs in nicotine-stimulated norepinephrine release from synaptosomes appears minimal or absent. It should be noted however that in hippocampal slice preparations a much larger percentage of norepinephrine is released by nicotine, e.g., ~700% over baseline (Sacaan et al., 1995) vs. the 41% over baseline (3 μM nicotine) or 176% (100 μM nicotine) release from hippocampal synaptosomal preparations reported in this and other studies (Clarke and Reuben, 1996). Nicotine-stimulated synaptosomal release of norepinephrine is not affected by the sodium channel blocker tetrodotoxin (Clarke and Reuben, 1996). In contrast, the majority of nicotine-stimulated norepinephrine release from hippocampal slices is blocked by tetrodotoxin (Sacaan et al., 1995), suggesting that at least some of the norepinephrine release is due to nAChRs not located on nerve terminals but dependent on voltage-gated sodium channels. It would be of interest in future studies to assess the effect of α-conotoxin MII on tetrodotoxin-sensitive and tetrodotoxin-insensitive nicotine-stimulated norepinephrine release.

Previous studies have had difficulty determining the specific subtypes of nAChRs involved in nicotine-stimulated dopamine release. Several factors have contributed to this difficulty. First, there is a lack of subtype-specific antagonists for neuronal nAChRs. One antagonist, a minor component of Bungarus venom known as κ-bungarotoxin, has been used with some success in the study of nicotine-stimulated dopamine release. Under certain conditions, κ-bungarotoxin preferentially blocks α3β2 receptors (Luetje et al., 1990), although the presence of venom purification contaminants has led to inconsistent findings (Fiordalisi et al., 1994). However, more recently it has been shown that κ-bungarotoxin blocks several subtypes of neuronal nAChRs, which was not initially appreciated due to the complex kinetics of this ligand (Papke et al., 1993). The ability of κ-bungarotoxin to selectively block α3β2 receptors or block multiple subtypes of nAChRs depending on the conditions used may help account for the reported differences in efficacy of this toxin in blocking nicotine-stimulated dopamine release.

Another approach has been to assess the potency of various nicotinic agonists stimulating dopamine release and compare these agonists to the potencies on nAChRs heterologously expressed in Xenopus oocytes. One complicating factor in this approach is the possibility that more than one subtype of nAChR underlies nicotine-stimulated dopamine release. In such a case, the potency of nicotinic agonists in stimulating dopamine release from brain tissue would not correlate with agonist potency with an individual nAChR subtype expressed in oocytes. A more complicated possibility is that native neuronal nAChRs are not simply a combination of a single type of α and β subunit. The muscle nAChR for example is a pentamer made up of four different subunits, α1β1δγ. Complicated receptors have also been shown to be present in neuronal tissue. For example, in chick ciliary ganglia 80% of the nAChRs have the subunit composition α3β4α5 and 20% have the subunit composition α3β2β4α5 (Conroy and Berg, 1996). The muscle nicotinic receptor requires two molecules of acetylcholine to bind prior to channel opening. The receptor-ligand binding sites are pharmacologically equivalent, being composed of an α1/δ and α1/γ interface. These two different interfaces have different affinities for agonists. Similarly, it has been shown that nAChRs with multiple α or β subunits have different affinities (Wang et al., 1996). Thus, the presence of such complex receptors in native tissue would not allow simple comparison of agonist potency with mono-α and mono-β combinations of nAChRs expressed in Xenopus oocytes.

Figure 6:
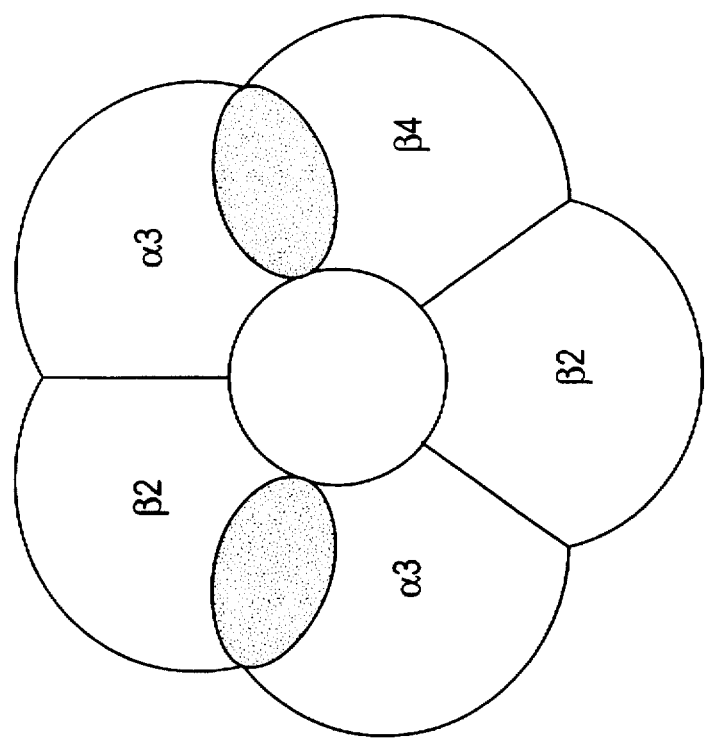
FIG. 6 is a diagram of a nicotinic AChR. Nicotinic AChRs can have non-symmetrical ligand binding sites. These binding sites are at the interface of a and non-α subunits. Since α-conotoxin MII discriminates between closely related ligand binding interfaces it serves as a specific probe for nAChRs which have an α3β2 interface as part of their subunit composition.

A particular advantage of α-conotoxin antagonists is their ability to discriminate between nonsymmetrical ligand binding interfaces present on the receptor. The best-studied example is α-conotoxin MI binding to the muscle nicotinic receptor. In mouse muscle, α-conotoxin MI displays a four order-of-magnitude selectivity for the α1/δ vs. the α1/γ binding site (Sine and Claudio, 1991). Nevertheless, α-conotoxin MI functionally blocks the muscle receptor with affinity comparable to its affinity for the α1/δ binding site, indicating that only one toxin molecule is required to prevent channel activation (Martinez et al., 1995). It was also recently demonstrated that α-conotoxin MII has two binding sites on α3β2 and α3β4 receptors expressed in Xenopus oocytes and only one toxin molecule is required to block function (Cartier et al., 1996b). α-Conotoxin MII discriminates between the α3/β2 and α3/β4 interface by four orders-of-magnitude. Thus, α-conotoxin MII has the ability to potently block any receptor containing an α3/β2 subunit interface regardless of what other α and β subunits may be present in the receptor complex. α-Conotoxin MII's potency at such receptors would still be high. A receptor containing only one α3β2 interface (see FIG. 6) would be expected to have an $IC_{50}$ approximately equal to the $K_d$.

Pharmaceutical compositions containing a compound of the present invention as the active ingredient can be prepared according to conventional pharmaceutical compounding techniques. See, for example, *Remington's Pharmaceutical Sciences*, 17th Ed. (1985, Mack Publishing Co., Easton, Pa.). Typically, an antagonistic amount of the active ingredient will be admixed with a pharmaceutically acceptable carrier. The carrier may take a wide variety of forms depending on the form of preparation desired for administration, e.g., intravenous, oral or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agents of the present invention are administered in an amount sufficient to generate the desired cardiovascular effect. The dosage range at which these agents exhibit this effect can vary widely, depending upon the severity of the patient's defect, the patient, the route of administration and the presence of other underlying disease states within the patient. A suitable dose can be administered in multiple sub-doses per day.

The present invention is further detailed in the following Examples which are offered by way of illustration and are not intended to limit the invention in any manner. Standard techniques well known in the art or the techniques specifically described below are utilized.

For the experiments described in the Examples, [$^3$H]-dopamine (~30 Ci/mmol) was purchased (as dihydroxyphenylethylamine, 3,4 [7-$^3$H]) from Dupont NEN, Boston, Mass. (#NET-131). [$^3$H]-Dopamine was aliquoted in 5 µCi amounts and stored under argon at −80° C. (−)Nicotine hydrogen tartrate was from Sigma (#N5260). Pargyline KCl (#D-026) and mecamylamine HCl (#M-106) were from Research Biochemicals International (Natick, Mass.). All drugs were prepared fresh in synaptosomal buffer (SB) prior to use. α-Conotoxin MII was synthesized as previously described (Cartier et al., 1996a). Male Sprague-Dawley rats, weighing 200–400 grams were maintained on a 12/12 hour light/dark cycle. Rats were housed three per cage, and food and water were available ad libitum. Rats were drug-naive at the start of each experiment.

EXAMPLE 1

Synaptosomal Preparation and [$^3$H]-Dopamine Preloading

Synaptosomes were prepared essentially as described by El-Bizri and Clarke (1994). For each experiment, two rats were decapitated and both striata (total wet tissue weight 180–240 mg) were immediately dissected on an ice-chilled platform and placed in dissection buffer (DB). Unless otherwise indicated, buffers used in the synaptosomal preparation were previously cooled to 4° C. The DB consisted of 0.32M sucrose, 5 mM HEPES adjusted to pH 7.5 with NaOH. Striata were homogenized in DB (0.02 mL/mg of wet tissue weight) using twelve up-and-down strokes at 900 rpm in a 0.25 mm clearance glass Teflon homogenizer. The homogenate was then centrifuged at 1000×g for 10 minutes at 4° C. The pellet was discarded and the supernatant was recentrifuged at 12,000×g for 20 minutes at 4° C. The final crude P2 synaptosomal fraction was resuspended in superfusion buffer (SB) (0.5 mL/100 mg wet tissue weight) containing 0.12 µM [$^3$H]-dopamine and incubated at 37° C. for 10 minutes. The synaptosomes were then centrifuged at 1000×g for 5 minutes at room temperature (24° C.) and the pellet was gently resuspended in 2.0 mL of SB. The superfusion buffer was composed of the following: 128 mM NaCl, 2.4 mM KCl, 3.2 mM CaCl$_2$, 1.2 mM KH$_2$PO$_4$, 0.6 mM MgSO$_4$, 25 mM HEPES, 10 mM D-glucose, 1 mM L-ascorbic acid, and 0.1 mM pargyline. BSA was included as a carrier protein at a final concentration of 0.1 mg/mL and the pH was adjusted to 7.5 with NaOH.

EXAMPLE 2

Superfusion

The assay system consisted of twelve identical channels. Each channel consisted of a length of Teflon TFE tubing (#5-8696, 0.8 mm ID, Supelco, Bellefonte, Pa.) connected to a three-way subminiature solenoid valve (#161T031, Neptune Research Inc., West Caldwell, N.J.), utilized to introduce buffer containing nicotine or 20 mM KCl. Teflon TFE tubing connected the solenoid valve to a stainless steel filter unit (#09-753-10A, Fisher) through a Teflon PTFE male luer adapter (#DN-06391-90, Cole-Parmer, Niles, Ill.). Thirteen mm diameter A/E glass fiber filters (#09-730-51, Fisher) were fitted within the filter units to suspend the synaptosomal preparation. Superfusate was continuously pulled downward through the filter units in platinum-cured silicon tubing (#H-96410-13, Cole-Parmer) at a rate of 0.5 mL/minute via a peristaltic pump (#H-07553-70, Cole-Parmer) positioned downstream. Teflon TFE tubing and Teflon-coated parts were utilized upstream of the synaptosomes to avoid plasticizers such as tinuvin 770 (a common light and radiation stabilizer used in a wide range of plastics) shown to block neuronal nAChRs (Papke et al., 1994).

The twelve-channel parallel assay system enabled several assays to be performed simultaneously. Before loading the synaptosomal preparation, channels were rinsed with distilled water and then superfusate buffer (SB alone or SB plus antagonist), with care taken to ensure that the tubing with superfusate buffer plus agonist (nicotine or KCl) was fully loaded up to the three-way solenoid switching valve. Two mL of the [$^3$H]-dopamine-loaded synaptosomes were diluted 4-fold with SB and pumped into the filtration apparatus.

Following a pre-collection superfusion period of 20 minutes, seventeen two-minute fractions per channel were collected into polypropylene minivials (#2060, Out Patient Services, Petaluma, Calif.) containing 4.0 mL of scintillation fluid (#88245305, Cytoscint, ICN Pharmaceuticals, Costa Mesa, Calif.). Following an initial collection period of 11–12 minutes, a 1 minute (0.5 mL) pulse of SB plus agonist or SB alone was delivered simultaneously to all channels by switching on the solenoids. Following the collection period, the filters holding the synaptosomes were removed to count residual radioactivity in a liquid scintillation counter (Beckman LS9800, 57.2% efficiency) along with the assay fractions.

EXAMPLE 3

Data Analysis

It has previously been shown that tritium released by nAChR agonists or by depolarizing amounts of KCl is equivalent to dopamine itself (Rapier et al., 1988). Throughout the Examples, tritium is assumed to correspond to dopamine release.

Release is calculated as: {cpm in the two peak fractions minus the average baseline release (average of two pre- and two post-release fractions)}/baseline release. Release is normalized as a percentage of total (agonist-stimulated) release. Results for each α-conotoxin MII concentration were compared to agonist-stimulated controls and analyzed for statistically significant mean differences using a paired, one-tailed t test on raw (non-normalized) data.

EXAMPLE 4

The Effects of α-Conotoxin MII on Nicotine-stimulated [$^3$H]-Dopamine Release

The ability of α-conotoxin MII to block nicotine-evoked [$^3$H]-dopamine release was assessed using rat striatal synaptosomes. As shown in FIG. 1, 3 μM nicotine stimulates the release of [$^3$H]-dopamine. This release is fully blocked by the non-selective, noncompetitive antagonist mecamylamine. The release is abolished in the absence of external calcium (not shown).

(−)-Nicotine has previously been shown to increase [$^3$H]-dopamine release from rat striatal synaptosomes in a concentration-dependent manner with an estimated EC$_{50}$ of $1.6 \times 10^{-7}$ M (El-Bizri and Clarke, 1994). α-Conotoxin MII blocked 3 μM nicotine-stimulated [$^3$H]-dopamine release with a nonsignificant trend toward block at 0.1 nM (P=0.08). At concentrations of 1 nM and above, α-conotoxin significantly blocked nicotine-evoked [$^3$H]-dopamine release in a dose-dependent manner (see FIG. 2). Concentrations of α-conotoxin MII of 10 nM and below are expected to be specific for α3β2 receptors (IC$_{50}$ 0.5 nM), whereas concentrations of 100 nM and 1 μM may have measurable effects on other nAChR subtypes (Cartier et al., 1996a; Cartier et al., 1996b).

EXAMPLE 5

Effect of α-Conotoxins Other than MII on Nicotine-stimulated Dopamine Release

α-Conotoxin MII is selective for the α3β2 subtype of nicotinic receptor. Structurally-related α-conotoxins which target non-α3β2 nicotinic subtypes were tested to determine whether they blocked nicotine-stimulated dopamine release (see Table I). α-Conotoxin MI, specific for the muscle subtype of nicotinic receptor and α-conotoxin ImI, specific for the α7 subtype of nicotinic receptor (Johnson et al., 1995) had no effect on release (FIG. 2).

TABLE I

| α-Conotoxin | Sequence | | nAChR Specificity |
|---|---|---|---|
| MII | GCCSNPVCHLEHSNLC* | (SEQ ID NO:1) | α3β2 |
| MI | GRCC—HPACGK—NYS—C* | (SEQ ID NO:2) | muscle |
| ImI | GCCSDPRC - - - AWRC* | (SEQ ID NO:3) | α7 |

EXAMPLE 6

Effects of α-Conotoxin MII on Depolarization-stimulated [$^3$H]-Dopamine Release To further investigate the specificity of effects of α-conotoxin MII, its effects on KCl-induced dopamine release were assessed. One hundred nM α-conotoxin MII, a concentration which blocks 33% of nicotine stimulated dopamine release, had no effect on potassium-stimulated dopamine release (FIG. 3).

EXAMPLE 7

Figure 5:
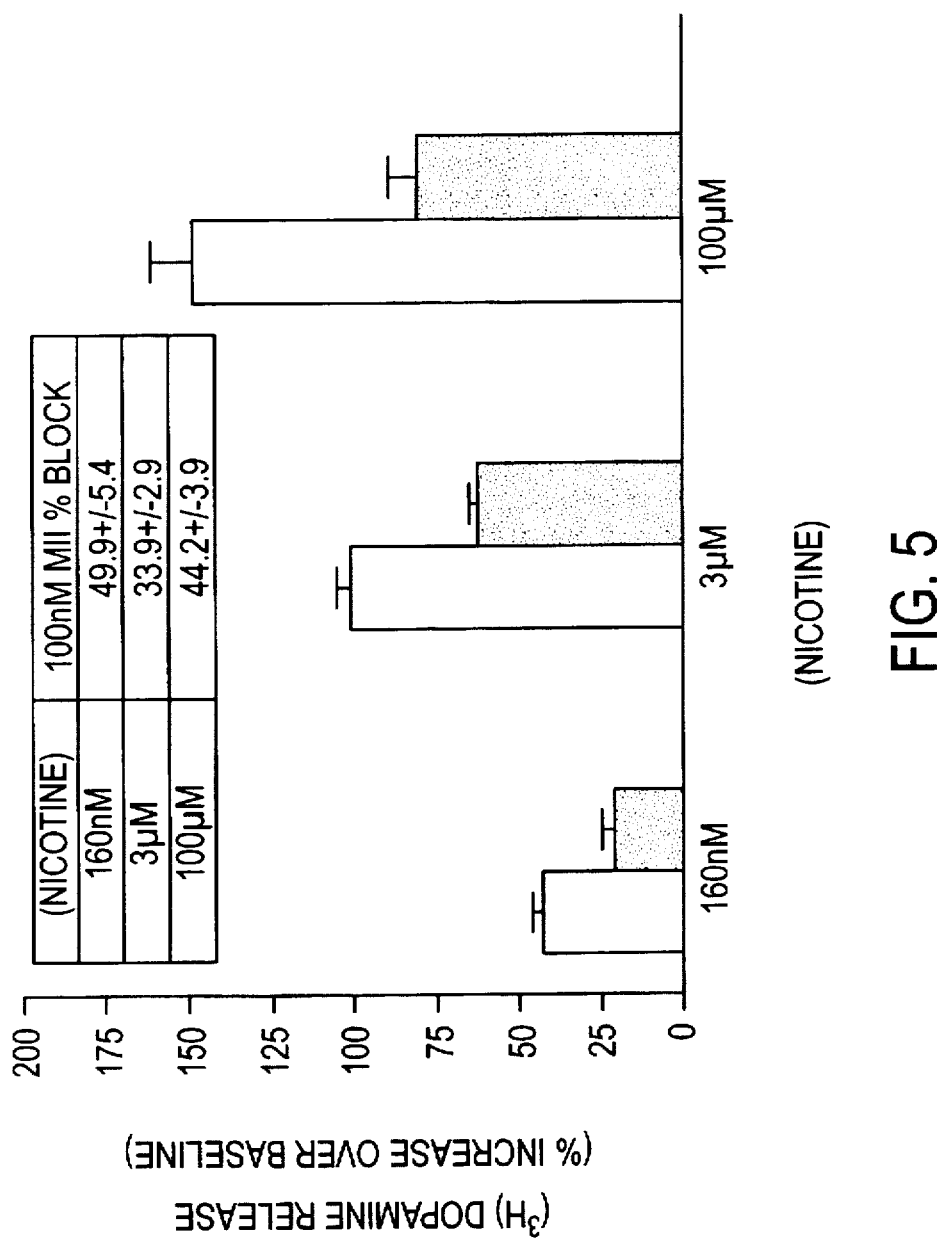
FIG. 5 shows that α-conotoxin MII blocks nicotine-stimulated dopamine release over a wide range of nicotine concentrations. The shaded bars indicate the addition of 100 nM MII.

Effects of α-Conotoxin MII on 100 μM Nicotine-stimulated [$^3$H]-Dopamine Release Previous investigators who have examined the effects of κ-bungarotoxin on nicotine-stimulated dopamine release have reported variable effects. One group reported a 50% inhibition of striatal dopamine release by 100 nM κ-bungarotoxin (Wonnacott et al., 1995). Other investigators have reported complete block of striatal dopamine release by 100 nM κ-bungarotoxin (Grady et al., 1992; Wilkie et al., 1993; Schultz and Zigmond, 1989). One difference between these studies is that the investigators who observed a 50% inhibition used 3 μM nicotine whereas the investigators who observed complete block used 50 or 100 μM nicotine. It has been suggested that at 3 μM, nicotine could be acting on a higher-affinity nicotinic receptor that has low sensitivity to κ-bungarotoxin whereas 50 to 100 μM nicotine is acting on a lower-affinity nAChR which has a high sensitivity to κ-bungarotoxin (Wonnacott et al., 1995). To more fully compare our results with previously reported results with κ-bungarotoxin, the effects of α-conotoxin MII on 160 nM, 3 μM and 100 μM-stimulated dopamine release were tested. One hundred nM α-conotoxin MII blocks 44% of 100 μM nicotine-stimulated [$^3$H]-dopamine release compared to 34% of 3 μM nicotine and 50% of 160 nM nicotine stimulated [$^3$H]-dopamine release as shown in FIG. 5.

EXAMPLE 8

Effects of α-Conotoxin MII on Nicotine-stimulated Norepinephrine Release

Figure 4:
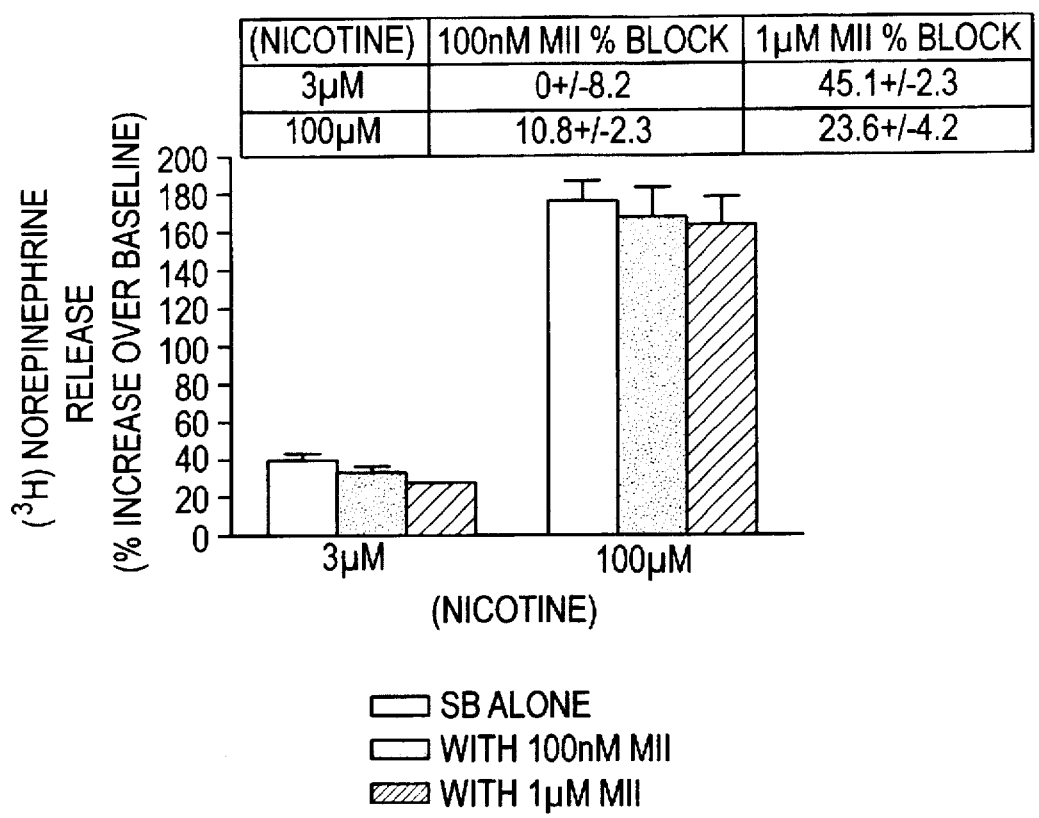
FIG. 4 shows [$^3$H]-norepinephrine release from synaptosomes. At low concentrations, α-conotoxin MII exhibits little, if any, block of nicotine-evoked norepinephrine release.

Nicotine evokes the release of [$^3$H]-norepinephrine in hippocampus (FIG. 4). It has previously been reported that nicotine releases striatal dopamine more potently than hippocampal norepinephrine (EC$_{50}$=0.16 μM vs. 6.5 μM) in synaptosomal preparations (Clarke and Reuben, 1996). Three μM nicotine was utilized to maximize the chance of seeing an effect by the competitive antagonist α-conotoxin MII. One hundred nM α-conotoxin MII blocked 0% of nicotine-stimulated norepinephrine release which was not statistically different from control. In contrast, 1 μM α-conotoxin MII blocked 45% (FIG. 4). α-Conotoxin MII was also tested on 100 μM nicotine-stimulated release. One hundred nM MII blocked 11% and 1 μM blocked 24%.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Adler, L. E. et al. (1993). Am. J. Psychiatry 150:1856–1861.
Cartier, G. E. et al. (1996a). J. Biol. Chem. 271:7522–7528.
Cartier, G. E. et al. (1996b). Soc. Neurosci. Abst. 22:268.
Clarke, P. B. S. and Reuben, M. (1996). Br. J. Pharmacol. 111:695–702.
Conroy, W. G. and Berg, D. K. (1996). J. Biol. Chem. 270:4424–4431.
El-Bizri, H. and Clarke, P. B. S. (1994). Br. J. Pharmacol. 111:406–413.
Fiordalisi, J. J. et al. (1994). Biochemistry 33:12962–12967.
Grady, S. et al. (1992). J. Neurochem. 59:848–856.
Grandinetii, A. et al. (1994). Am. J. Epidemiol. 139:1129–1138.
Gray, R. et al. (1996). J. Neurochem. 59:848–856.
Janson, A. M. et al. (1988). Acta Physiologica Scandinavica 132:589–591.
Johnson, D. S. et al. (1995). Mol. Pharmacol. 48:194–199.
Lapchak, P. A. et al. (1989). J. Neurochem. 52:483–491.

Luetje, C. W. et al. (1990). J. Neurochem. 55:632–640.
Luntz-Leybman, V. et al. (1992). Brain Res. 587:130–136.
Martinez, J. S. et al. (1995). Biochemistry 34:14519–14526.
McGehee, D. S. and Role, L. W. (1995). Annu. Rev. Physiol. 57:521–546.
Mulle, C. et al. (1991). J. Neurosci 11:2588–2597.
Nordberg, A. et al. (1990). J. Neural Transm. (P-D Sect.) 2:215–224.
Nordberg, A. et al. (1989). Progr. Brain Res. 79:353–362.
Papke, R. L. et al. (1994). J. Pharmacol. Exp. Ther. 268:718–726.
Papke, R. L. et al. (1993). Proc. R. Soc. Lond. B 252:141–148.
Rapier, C. et al. (1988). J. Neurochem. 50:1123–1130.
Reavill, C. (in press). "Action of nicotine on dopamine pathways and implications for Parkinson's disease". Oxford University Press.
Rowell, P. P. and Winkler, D. L. (1984). J. Neurochem 43:1593–1598.
Sacaan, A. I. et al. (1995). J. Pharmacol. Exp. Therapeutics 274:224–230.
Sandberg, P. R. et al. (1988). Lancet March 12:592.
Sandberg, P. R. et al. (1989). Biomed. & Pharmacother. 43:19–23.
Schatzberg, A. F., Nemeroff, C. B. and eds. (in press). "Section II: Classes of psychiatric drugs: animal and human pharmacology" American Psychiatric Press, Inc.
Schultz, D. W. and Zigmond, R. E. (1989). Neurosci. Lett. 98:310–316.
Sine, S. M. and Claudio, T. (1991). J. Biol. Chem. 266:19369–19377.
Stolerman, I. P. and Jarvis, M. J. (1995). Psychopharmacology 117:2–10.
Vidal, C. and Changeux, J. P. (1993). Neuroscience 56:23–32.
Wang, F. et al. (1996). J. Biol. Chem. 271:17656–17665.
Wilkie, G. I. et al. (1993). Biochem. Soc. Trans. 21:429–431.
Wonnacott, S. et al. (1995). "Presynaptic nicotinic autoreceptors and heteroreceptors in the CNS". In *Effects of Nicotine on Pharmacological Systems II*, P. B. S. Clarke et al. (eds.) (Basel, Switzerland: Birkhäuser Verlag), pp. 87–94.

What is claimed is:

1. A method to aid a person who smokes nicotine containing products to quit smoking said nicotine containing products wherein said method comprises a step of administering $\alpha$-conotoxin MII to said person wherein said $\alpha$-conotoxin MII is administered in an amount which is effective to aid said person to quit smoking said nicotine containing products.

2. The method of claim 1 wherein $\alpha$-conotoxin MII is administered to yield a cerebrospinal fluid concentration greater than 0.1 nM.

3. The method of claim 1 wherein $\alpha$-conotoxin MII is administered to yield a cerebrospinal fluid concentration in the range 0.1–1000.0 nM.

4. The method of claim 1 wherein $\alpha$-conotoxin MII is administered to yield a cerebrospinal fluid concentration in the range 1.0–1000.0 nM.

5. The method of claim 1 wherein $\alpha$-conotoxin MII is administered to yield a cerebrospinal fluid concentration in the range 1.0–10.0 nM.

* * * * *